(12) United States Patent
Cartellone

(10) Patent No.: US 6,511,531 B1
(45) Date of Patent: Jan. 28, 2003

(54) ROOM AIR FILTERING AND FRESHENING DEVICE

(75) Inventor: Mark A. Cartellone, Broadview Hts, OH (US)

(73) Assignee: HMI Industries, Inc., Seven Hills, OH (US)

( * ) Notice: Subject to any disclaimer, the term of this patent is extended or adjusted under 35 U.S.C. 154(b) by 16 days.

(21) Appl. No.: 09/769,820

(22) Filed: Jan. 26, 2001

(51) Int. Cl.[7] .................................................. B01F 3/04
(52) U.S. Cl. ........................... 96/222; 261/30; 261/142; 261/DIG. 88; 261/DIG. 89; 55/414
(58) Field of Search .............................. 96/222; 261/30, 261/104, DIG. 88, DIG. 89, 142; 422/124; 55/414

(56) References Cited

U.S. PATENT DOCUMENTS

| 1,891,256 A | * 12/1932 | Bilde ..................... 15/DIG. 8 |
| 1,921,085 A | 8/1933 | Korittke |
| 2,033,833 A | 3/1936 | Kent |
| 2,098,072 A | 11/1937 | Taylor |
| 2,139,736 A | 12/1938 | Durham |
| 2,242,278 A | 5/1941 | Yonkers, Jr. |
| 2,308,682 A | 1/1943 | Fuge |

(List continued on next page.)

FOREIGN PATENT DOCUMENTS

| DE | 27 11 111 A1 | 9/1979 |
| DE | 42 40 172 A1 | 6/1994 |
| FR | 2 653 354 A1 | 4/1991 |
| JP | 2-187114 A2 | 7/1990 |
| JP | 4-197460 A2 | 7/1992 |
| JP | 8-66341 A2 | 3/1996 |
| JP | 11-309204 A2 | 11/1999 |

OTHER PUBLICATIONS

Article entitled 3M Brand Substrate Blown Microfiber Filter Media, from brochure entitled *3M Filtration Products*, 1994.

*Primary Examiner*—Robert A. Hopkins
(74) *Attorney, Agent, or Firm*—Fay, Sharpe, Fagan, Minnich & McKee

(57) ABSTRACT

An air filtering and freshening device comprising a filter element within the intake of the device housing, a motorized fan mounted within the device housing which draws contaminated air into the device, and forces air out of the device through an outlet having separate exhaust and scent discharge passages. The exhaust passage including a plurality of arcuate vanes radiating outwardly from the interior of the device, and being disposed across the exhaust passage to promote efficient operation by reducing the pressure drop through the passage and minimizing operational noise. The scent discharge passage includes a scent element producing a freshening scent. The scent element is removably positioned adjacent the scent discharge passage, which carries high velocity, high pressure filtered air from the motorized fan, picks up the concentrated freshening scent, and discharges in an effective and efficient manner, a continuous stream of freshening scent.

30 Claims, 15 Drawing Sheets

U.S. PATENT DOCUMENTS

| | | |
|---|---|---|
| 2,362,933 A | 11/1944 | Schaefer |
| 2,394,923 A | 2/1946 | Little |
| 2,587,991 A | 3/1952 | Gerber |
| 2,608,268 A | 8/1952 | Gerber |
| 2,627,936 A | 2/1953 | Martinet |
| 2,627,937 A | 2/1953 | Martinet |
| 2,763,886 A | 9/1956 | Brown, Jr. et al. |
| 3,343,344 A | 9/1967 | Fairaizl et al. |
| 3,426,512 A | 2/1969 | Nesher |
| 3,498,032 A | 3/1970 | Scott |
| 3,500,517 A | 3/1970 | Dekker et al. |
| 3,545,181 A | 12/1970 | Young |
| 3,608,024 A | 9/1971 | Yazawa et al. |
| 3,616,624 A | 11/1971 | March |
| 3,724,181 A | 4/1973 | Benson, Jr. |
| 3,804,942 A | 4/1974 | Kato et al. |
| 3,853,512 A | 12/1974 | Hayashi |
| 3,870,495 A | 3/1975 | Dixson et al. |
| 3,925,043 A | 12/1975 | Matrone et al. |
| 3,953,184 A | 4/1976 | Stockford et al. |
| 3,966,597 A | 6/1976 | Omori et al. |
| 3,998,916 A | 12/1976 | van Turnhout |
| 4,121,916 A | 10/1978 | Fricke |
| 4,229,193 A | 10/1980 | Miller |
| 4,252,547 A | 2/1981 | Johnson |
| 4,339,250 A | 7/1982 | Thut |
| 4,361,427 A | 11/1982 | Barradas |
| 4,365,980 A | 12/1982 | Culbert et al. |
| 4,374,888 A | 2/1983 | Bornslaeger |
| 4,377,399 A | 3/1983 | Bryson |
| 4,378,234 A | 3/1983 | Suzuki et al. |
| 4,385,911 A | 5/1983 | Popeil et al. |
| 4,477,270 A | 10/1984 | Tauch |
| 4,504,290 A | 3/1985 | Pontius |
| 4,507,819 A | 4/1985 | Martinec |
| 4,514,197 A | 4/1985 | Armbruster |
| 4,531,956 A | 7/1985 | Howorth |
| 4,541,847 A * | 9/1985 | Oie et al. ..................... 55/467 |
| 4,627,862 A | 12/1986 | Frei et al. |
| 4,629,482 A | 12/1986 | Davis |
| 4,650,505 A | 3/1987 | Magdelain |
| 4,687,579 A | 8/1987 | Bergman |
| 4,687,697 A | 8/1987 | Cambo et al. |
| 4,695,434 A | 9/1987 | Spector |
| 4,702,753 A | 10/1987 | Kowalczyk |
| 4,737,173 A | 4/1988 | Kudirka et al. |
| 4,749,390 A | 6/1988 | Burnett et al. |
| 4,750,924 A | 6/1988 | Potter |
| 4,784,676 A | 11/1988 | Hale |
| 4,810,269 A | 3/1989 | Stackhouse et al. |
| 4,874,659 A | 10/1989 | Ando et al. |
| 4,886,527 A | 12/1989 | Föttinger et al. |
| 4,900,344 A | 2/1990 | Lansing |
| 4,900,437 A | 2/1990 | Savall |
| 4,902,306 A | 2/1990 | Burnett et al. |
| 4,904,343 A | 2/1990 | Giglia et al. |
| 4,909,815 A | 3/1990 | Meyer |
| 4,917,942 A | 4/1990 | Winters |
| 4,921,510 A | 5/1990 | Plooy |
| 4,927,437 A | 5/1990 | Richerson |
| 5,037,455 A | 8/1991 | Scheineson et al. |
| 5,108,470 A | 4/1992 | Pick |
| 5,141,706 A | 8/1992 | Clark |
| 5,188,646 A | 2/1993 | Nolen, Jr. |
| 5,221,573 A | 6/1993 | Baigas, Jr. |
| 5,240,478 A | 8/1993 | Messina |
| 5,248,323 A | 9/1993 | Stevenson |
| 5,273,487 A | 12/1993 | Dauvergne |
| 5,287,591 A | 2/1994 | Rench et al. |
| 5,288,298 A | 2/1994 | Aston |
| 5,290,330 A | 3/1994 | Tepper et al. |
| 5,306,534 A | 4/1994 | Bosses |
| 5,307,538 A | 5/1994 | Rench et al. |
| 5,350,443 A | 9/1994 | von Blücher et al. |
| 5,350,620 A | 9/1994 | Sundet et al. |
| 5,358,443 A | 10/1994 | Mitchell et al. |
| 5,399,319 A | 3/1995 | Schoenberger et al. |
| 5,435,817 A | 7/1995 | Davis et al. |
| 5,443,625 A | 8/1995 | Schaffhausen |
| 5,478,377 A | 12/1995 | Scavnicky et al. |
| 5,498,272 A | 3/1996 | Leon |
| 5,515,573 A | 5/1996 | Frey |
| 5,547,616 A * | 8/1996 | Dancs et al. ................. 261/100 |
| 5,562,407 A * | 10/1996 | Cielo ...................... 415/121.2 |
| 5,593,479 A | 1/1997 | Frey et al. |
| 5,603,741 A | 2/1997 | Frey |
| 5,641,343 A | 6/1997 | Frey |
| 5,647,881 A | 7/1997 | Zhang et al. |
| 5,651,811 A | 7/1997 | Frey et al. |
| 5,658,362 A | 8/1997 | Frey |
| 5,735,918 A | 4/1998 | Barradas |
| 5,837,020 A | 11/1998 | Cartellone |
| 5,840,103 A | 11/1998 | Dyson |
| 5,874,052 A | 2/1999 | Holland |
| 5,911,742 A * | 6/1999 | Akazawa ..................... 165/41 |
| 5,931,991 A | 8/1999 | Leon |
| 6,003,196 A | 12/1999 | Wright et al. |
| 6,010,550 A | 1/2000 | Song |
| 6,024,783 A * | 2/2000 | Budman ..................... 261/104 |
| 6,090,184 A | 7/2000 | Cartellone |
| 6,197,096 B1 | 3/2001 | Cartellone |
| 6,243,915 B1 | 6/2001 | Nakai et al. |
| 6,341,579 B1 * | 1/2002 | Alkire et al. ............... 119/165 |

\* cited by examiner

ROOM AIR FILTERING AND FRESHENING DEVICE

INCORPORATION BY REFERENCE

Johnson, U.S. Pat. No. 4,252,547; Barradas, U.S. Pat. No. 5,735,918; and Cartellone, U.S. Pat. No. 5,837,020 are incorporated herein by reference, so that background art relating to air filtering and freshening devices need not be described in detail herein.

BACKGROUND OF THE INVENTION

This invention relates to the art of air filtering devices and, more particularly, to devices which both filter pollutants from contaminated air and introduce a freshening scent to the filtered air.

Air filtering and freshening devices have been provided heretofore and generally, as shown in patents to Barradas (U.S. Pat. No. 5,735,918) and Johnson (U.S. Pat. No. 4,252,547) for example, have a fan for moving air through the device, a filtering element for removing pollutants from contaminated air, and a freshening device for adding a scent to the air. These existing devices also include a housing, within which each of the other components is situated. In the air filtering and freshening devices provided heretofore, the relative position of each of the components in the housing has led to inefficient and ineffective performance of these devices.

For example, in Barradas the fan is positioned within the housing upstream of the filter element. That is, the fan pushes the air into and through the filter element. As a result, the air exiting the filter element has a relatively low velocity and therefore does not circulate effectively. Furthermore, as the filter element becomes increasingly filled with contaminants, it is increasingly difficult for air to pass through the device. This means that the velocity of the already low velocity air being discharged from the device is further reduced as the filter element becomes increasingly dirty. Furthermore, the scent discharged in Barradas is fed by both filtered and unfiltered air due to its position in the housing relative to the filter element. As a result of this dual air feed, some contaminated or unfiltered air is output by the device. As the filter element becomes increasingly dirty and it becomes increasingly more difficult for air to pass through, so more and more unfiltered air is fed to the scent discharge and recycled into the surrounding air. Another problem with positioning the fan before the filter element is that this results in dirt and dust collecting on the motor and which dramatically reduces its service life. Finally, air flows from areas of higher pressure to areas of lower pressure. By positioning the fan upstream of the filter element, Barradas uses atmospheric pressure as the lower pressure area. Barradas therefore requires the fan to generate high pressure air having a value greater than the atmospheric pressure plus the pressure loss across the filter element. Otherwise, no air will flow through the device. This is an inefficient arrangement which creates power requirements significantly higher than are necessary.

In contrast to Barradas, Johnson positions the fan downstream of the filter elements. This makes for a more efficient use of the fan by utilizing atmospheric pressure to induce flow of air to the low pressure area created by the fan on the other side of the filter element. This arrangement also permits filtered air rather than unfiltered air to pass across the motor, eliminating the dirt and dust build up which shortens motor life. However, Johnson, like Barradas, does allow some unfiltered air to pass through and be output by the device. Converse Barradas, which has a single intake passage and dual output passages, Johnson has dual intake passages that feed a single output chamber. The first of the Johnson intakes is through a filter element in the conventional manner. The second intake flows parallel to the first but does not include a filter element. The second air intake allows air to flow into a scent chamber without being filtered. The freshened scent is introduced to the unfiltered air in the chamber and then the air is discharged into a main exhaust chamber which also contains filtered air that is flowing toward the output.

Along with the circulation of unfiltered air, another problem left unresolved by the device of Johnson is the ineffective discharge of the freshening scent. As discussed above, the device in Johnson draws unfiltered air into and through the scent chamber. The freshened air is then drawn into an exhaust chamber where it may get caught in an eddy which could retain the air in the device, or it may be diffused into the surrounding air, or it may be immediately expelled in its concentrated form. As the flow of air within the device dynamically changes, the freshened air will likely move between each of these three discharge flows. As a result, the scent output of the device in Johnson is not consistent, and a scent output control will not be effective in controlling the output of the freshening scent.

SUMMARY OF THE INVENTION

In accordance with the present invention, an air filtering and freshening device of the foregoing character is provided which avoids or minimizes the problems and inefficiencies encountered with the use thereof. More particularly in this respect, an air filtering and freshening device is provided which effectively and efficiently produces filtered and freshened air without recycling any unfiltered air. Furthermore, the air filtering and freshening device of the subject invention discharges freshened air in a consistent and effective manner which is responsive to the scent discharge control baffle.

The subject invention provides a motorized fan within the housing of the air filtering and freshening device that "pulls" contaminated air through the filter element and into the housing by creating a lower pressure area inside the housing, adjacent the filter element. The higher pressure of the atmosphere outside the housing causes contaminated air to flow through the filter element to the lower pressure area within the housing, thereby filtering the contaminated air. This is an efficient use of the naturally occurring atmospheric pressure, which utilizes this pressure to create flow through the device rather than working to create flow against the atmospheric pressure. The fan then "pushes" the filtered air out of the outlet of the housing through both an exhaust passage and a scent discharge passage.

Both the exhaust and scent discharge passages are in direct fluid communication with the motorized fan, whereby the flow of filtered and freshened air from the respective passages is not affected by the condition of the intake filter element in the drastic manner that prior filtering devices have been. Furthermore, the filtered air is "pushed" through the freshening device by the fan providing high velocity, filtered air concentrated with scent to be output through the scent discharge passage. This scented air is then dispersed into the surrounding atmosphere in a consistent and effective manner, regulated only by the control baffle, and without being influenced by the condition of the filter element or an inefficient flow through the house. The scent output is further enhanced by the provision of a heating element adjacent the scent element which increases the concentration of scent output.

Due to the increased effectiveness of the freshening device and the desire to maintain such effectiveness, the regular replacement of the scent element is important. Accordingly, the subject invention provides easy access to the scent element which can be removed and replaced without the use of tools. The scent element is secured within a drawer which is spring biased toward an ejected position, in which the scent element is accessible and easily replaced. By pushing the drawer against the spring bias, the drawer will return to a retracted position in which the replaced scent element is again in position to dispense freshening scent into the flowing air. If the drawer is pushed against the bias of the spring a second time, the drawer will release and the spring will bias the drawer toward the ejected position, again providing access to the scent element. As previously indicated, this is accomplished without the use of or need for tools.

Accordingly, it is one of the main objects of the present invention to provide a high efficiency air filter having a freshening device therein which can be adjusted to control the scent output without restricting the exhaust of filtered air.

Another object of the present invention is the provision of an air filtering and freshening device in which the volumetric flow of scented air is not directly influenced by the condition of the filter element.

Still another object of the present invention is the provision of an air filtering and freshening device in which the freshening device has simple controls that can be easily adjusted between a no output position and a full output position.

A further object of the invention is the provision of an air filtering and freshening device having a scent element within the freshening device which is easily accessible and replaceable without the use of or need for tools.

Yet another object of the invention is to provide an air filtering and freshening device in which the effectiveness of the scent freshening element is improved.

A further object is the provision of an air filtering and freshening device which is comprised of a minimum number of parts and is structurally simple, thereby promoting economical production of the device.

BRIEF DESCRIPTION OF THE DRAWINGS

The foregoing objects, and others, will in part be obvious and in part pointed out more fully hereinafter in conjunction with the written description of preferred embodiments of the invention illustrated in the accompanying drawings in which.

DESCRIPTION OF THE PREFERRED EMBODIMENTS

Figure 1:
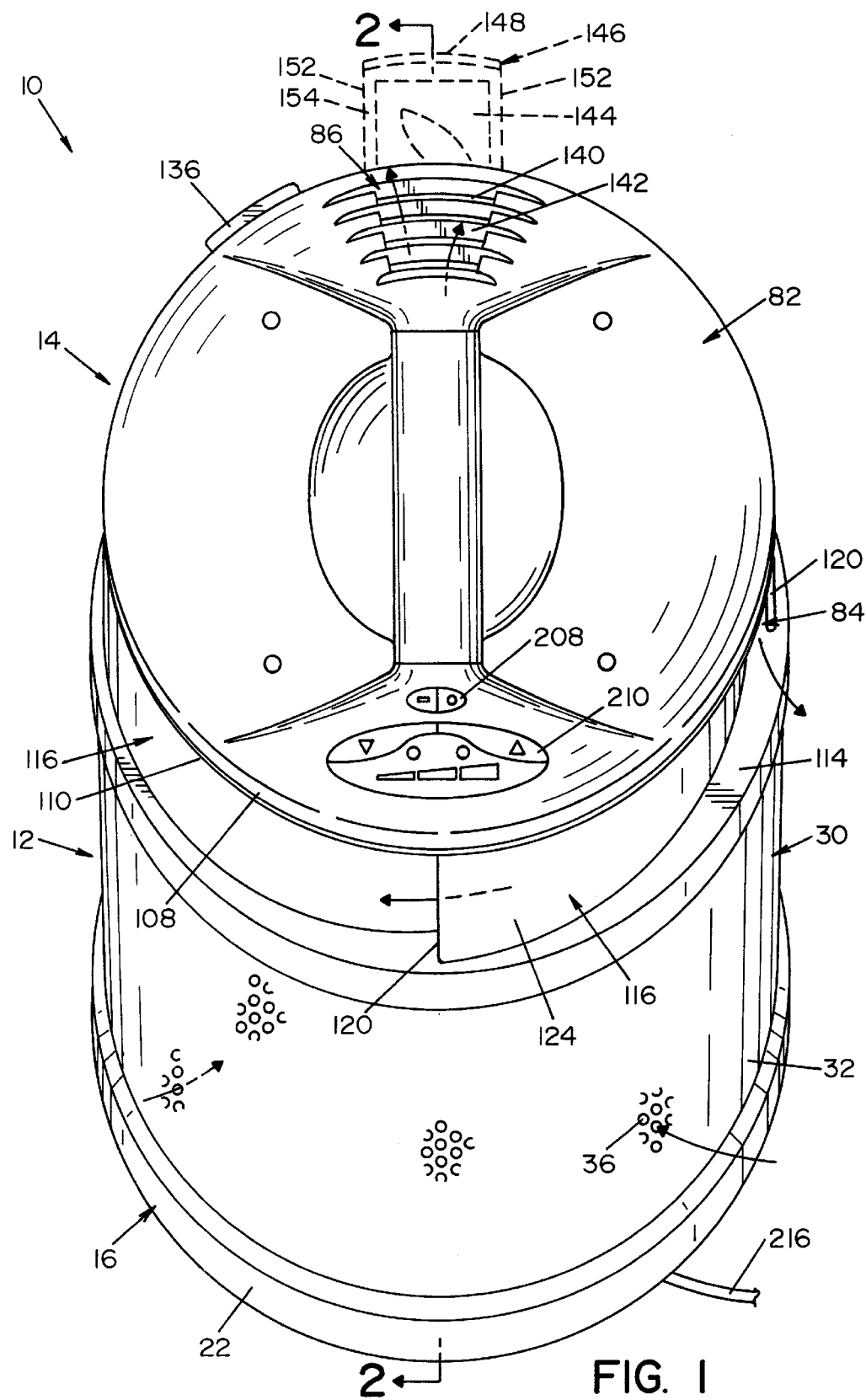
FIG. 1 is a perspective view of one embodiment of an air filtering and freshening device in accordance with the present invention.
Figure 2:
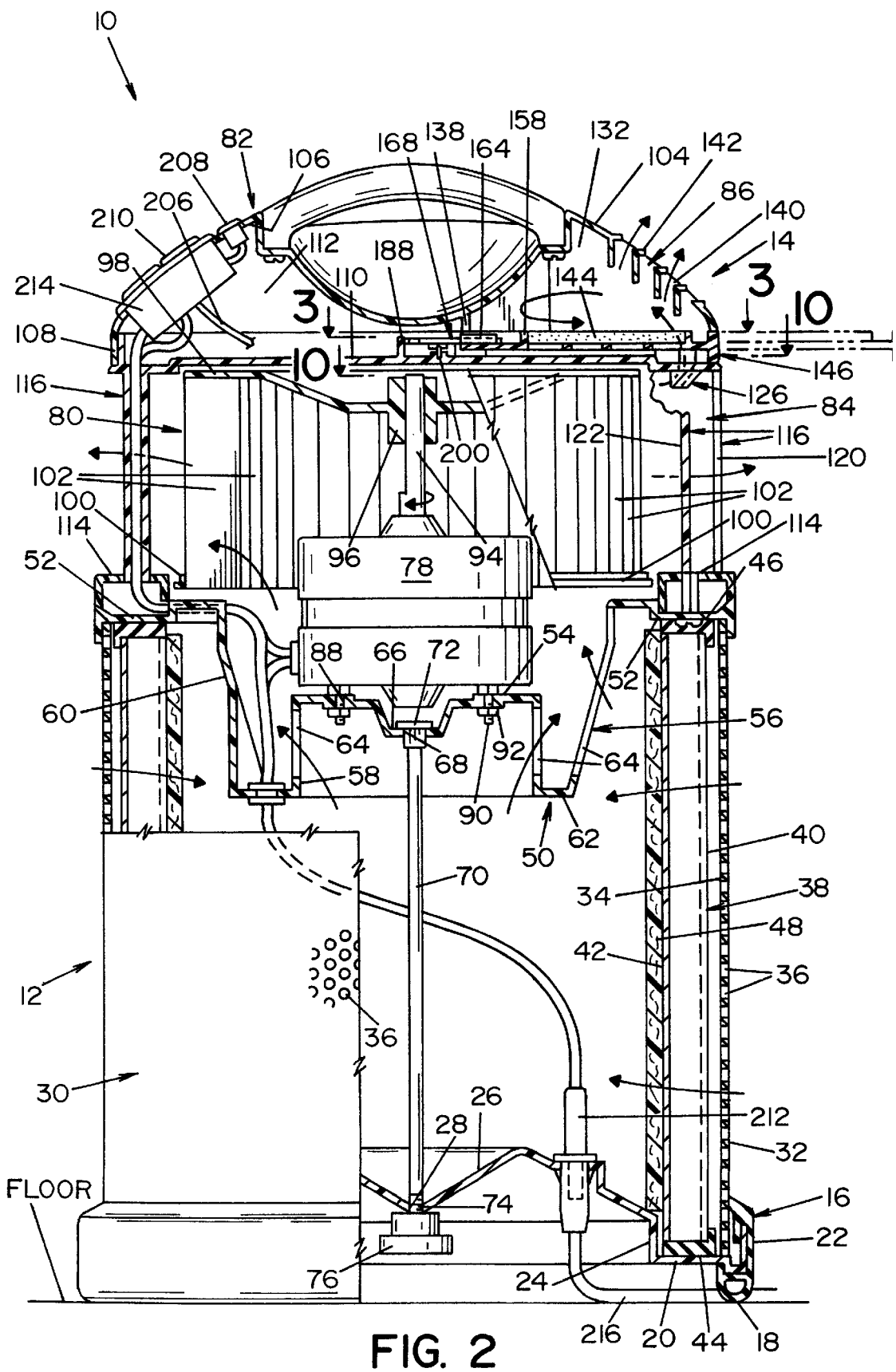
FIG. 2 is a sectional elevation view taken along line 2—2 in FIG. 1.
Figure 3:
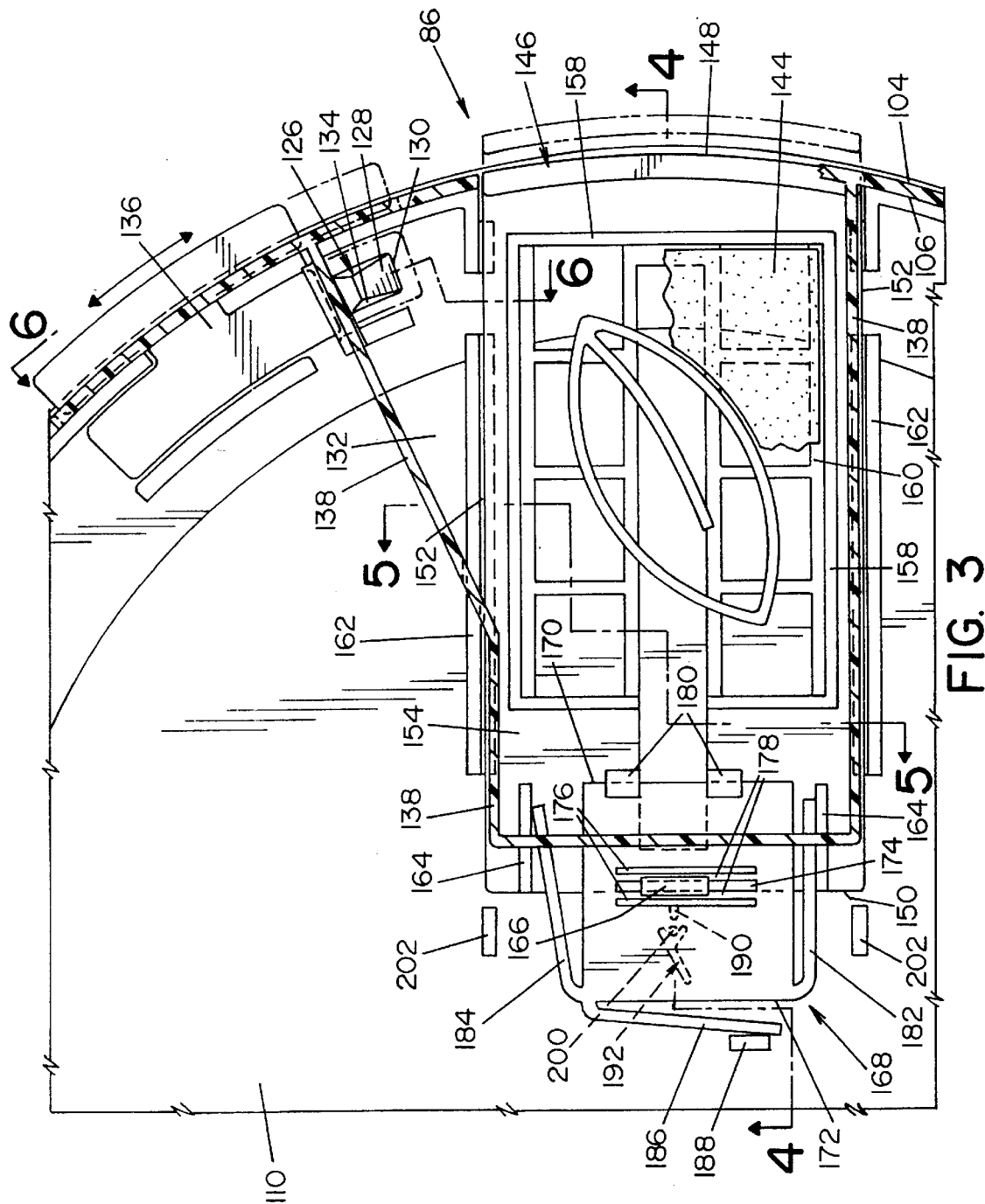
FIG. 3 is a partial sectional top plan view taken along line 3—3 of FIG. 2.

Referring now in greater detail to the drawings, wherein the showings are for the purpose of illustrating preferred embodiments of the invention only, and not for the purpose of limiting the invention, FIGS. 1 and 2 of the drawings illustrate an air filtering and freshening device 10 having a lower housing portion 12 and an upper housing portion 14. Lower housing portion 12 includes a base 16 having a bottom surface 18 resting upon the floor of an interior space of a building; filter support surface 20 parallel with but spaced away from bottom surface 18; an outside radial wall 22 extending upwardly from filter support surface 20 in the direction away from bottom surface 18; an inside radial wall 24 spaced radially inwardly from outside radial wall 22; and a guide surface 26 in the center of base 16 extending to inside radial wall 24 and having a hole 28 axially therethrough.

Resting on filter support surface 20 is a screen 30 of cylindrical shape having a screen outside surface 32 that fits within inside radial wall 22. Screen 30 has a relatively limited thickness forming a screen inside surface 34 having a diameter slightly less than screen outside surface 32. Screen material is well known, and is available in a wide variety of sizes and constructions, and therefore will not be further described hereinafter except to indicate that the construction of the screen material and the relative size of mesh holes 36 should be selected based on the application and atmosphere in which the device will operate. In making such a selection, mesh holes 36 should be of sufficient size that air can pass relatively freely through the screen yet mesh holes 36 should be small enough to prevent larger objects from passing through the screen and damaging the filter element 38.

Filter element 38 is cylindrical in shape having a filter outside surface 40 and a filter inside surface 42. Filter element 38 extends axially from a first filter end 44 to a second filter end 46. Filter element 38 fits axially within screen 30 so that first filter end 44 is resting on and supported by filter support surface 20, and filter inside surface 42 is adjacent inside radial wall 24. Filter element 38 can be constructed of any one, or more than one, of a wide variety of particle filter materials depending on the application in which the filter is intended to operate. Filter materials of this kind are well known, and therefore will not be further described hereinafter. However, a supplemental carbon filter 48 can be optionally fit axially within and adjacent filter inside surface 42 of filter element 38 to further remove smoke and other gas particles.

Filter element 38 is axially captured between filter support surface 20 adjacent first filter end 44, as previously indicated, and motor mount support surface 52 which is axially adjacent and supported by second filter end 46 of filter element 38. Motor mount support surface 52 extends radially outwardly from the center of motor mount 50, and is connected to motor support surface 54 by a transfer structure 56 which extends therebetween. Transfer structure 56 consists of two generally axially extending cylindrical transfer walls 58 and 60 connected by a bottom 62 which extends radially therebetween. Transfer wall 60 is connected to motor mount support surface 52, and transfer wall 58 extends from motor support surface 54. Both transfer walls 58 and 60 have a series of transfer passages 64 extending therethrough which permit incoming filtered air in the lower housing portion 12 to be in fluid communication with upper housing portion 14. Recessed axially from motor support surface 54 is tension rod surface 66 which has a hole 68 axially therethrough. Tension rod 70 passes through hole 68 and tension rod surface 66 and extends into hole 28 in guide surface 26 of base 16. End cap 72 of tension rod 70 is forced against tension rod surface 66 as a knob 76 is threaded onto the threaded end 74 of tension rod 70, thereby tensioning tension rod 70 and compressibly capturing filter element 38 between filter support surface 20 and motor mount 25 support surface 52.

Upper housing portion 14 extends from motor mount 50 and includes a motor 78, a centrifugal fan 80 driveably connected to motor 78, and a cover 82. Motor 78 is attached to motor support surface 54 by a plurality of threaded mounting studs 90 which extend through corresponding mounting holes 88 and are secured by threaded nuts 92. Motor 78 has a drive shaft 94 extending axially therefrom in the direction opposite to threaded mounted studs 90. Centrifugal fan 80 has a hub 96 driveably attached to drive shaft 94. Hub 96 is connected to upper rim 98 of centrifugal fan 80. Lower rim 100 is axially spaced from upper rim 98 toward motor 78, and a plurality of fan blades 102 extend therebetween in a radial pattern coaxial with hub 96.

Cover 82 is axially spaced away from motor 78 in the direction opposite base 16, and has a cover exterior surface 104, a cover interior surface 106, and a baffle mounting plate 110 which is adjacent upper rim 98 of centrifugal fan 80. The exterior and interior surfaces 104 and 106 of cover 82 provide a generally curvilinear thin-walled shell that terminates at cover rim 108. Baffle mounting plate 110 is attached to cover 82 adjacent cover rim 108, defining a cavity 112 between cover interior surface 106 and baffle mounting plate 110.

As previously discussed, cover 82 is axially spaced away from motor mount 50 such that baffle mounting plate 110 is adjacent upper rim 98 of centrifugal fan 80. On the opposite side of motor mount support surface 52 on motor mount 50 is a radially extending vane mount surface 114. A plurality of outwardly radiating arcuate vanes 116 extend axially from baffle mounting plate 110 and are attached to vane mount surface 114 of motor mount 50. As is more clearly shown in FIG. 10, arcuate vanes 116 each have a leading edge 118 and the trailing edge 120. Leading edges 118 are equidistantly disposed around the perimeter of centrifugal fan 80. Trailing edges 120 of arcuate vanes 116 are positioned radially outwardly of leading edges 118 and are equidistantly spaced adjacent the perimeter of vane mount surface 114 and baffle mounting plate 110. As is more fully discussed in Cartellone ('020), which has been incorporated herein by reference, the length, curvature, and quantity of arcuate vanes 116 in any particular embodiment of the subject device will depend on the overall size of the outside diameter of the air filtering and freshening device 10 and the output capacity for which the device was designed. The flow of the filtered air between arcuate vanes 116 as the air is output by device 10 is more fully described hereinafter.

As can be appreciated from the discussion hereinbefore, centrifugal fan 80 "pulls" contaminated air into air filtering and freshening device 10 through filter element 38, and then "pushes" the filtered air out of the device 10 through exhaust passage 84 and scent discharge passage 86. Exhaust passage 84 extends radially from the periphery of centrifugal fan 80 and is axially defined by baffle mounting plate 110 and vane mount surface 114 of motor mount 50. Exhaust passage 84 is made up of a plurality of individual passages corresponding to and defined as the space between arcuate vanes 116. The filtered air is "pushed" by centrifugal fan 80 uniformly through each of the individual passages, collectively defining exhaust passage 84, so that the filtered air flows along both concave side 122 and convex side 124 of each of the arcuate vanes 116. However, as the filtered air is forced radially outwardly by blades 102 of centrifugal fan 80 the filtered air is compressed against the concave side 122 of arcuate vanes 116. This action creates high pressure filtered air that travels radially along the concave side 122 of arcuate vanes 116 until the air reaches the leading edge 118 of the next adjacent arcuate vane 116. After the filtered air travels beyond the leading edge 118 of the next adjacent arcuate vane 116, the high pressure filtered air thereafter travels between the radially extending arcuate vanes 116 until the air is discharged from device 10. As the air travels between the two adjacent arcuate vanes 116, the high pressure air expands as the adjacent arcuate vanes 116 move further apart, decreasing the air pressure and increasing its velocity. This results in high velocity air being discharged from air filtering and freshening device 10 through exhaust passage 84. At any point along the flow of air between adjacent arcuate vanes 116 of exhaust passage 84, a pressure and velocity gradient will exist transverse to the direction of flow. Diversion channel 126, more fully described hereinafter, should be positioned relative to arcuate vanes 116 so that high pressure and high velocity air can be diverted into scent chamber 132, thereby improving the effectiveness of scent discharge passage 86.

Figure 10:
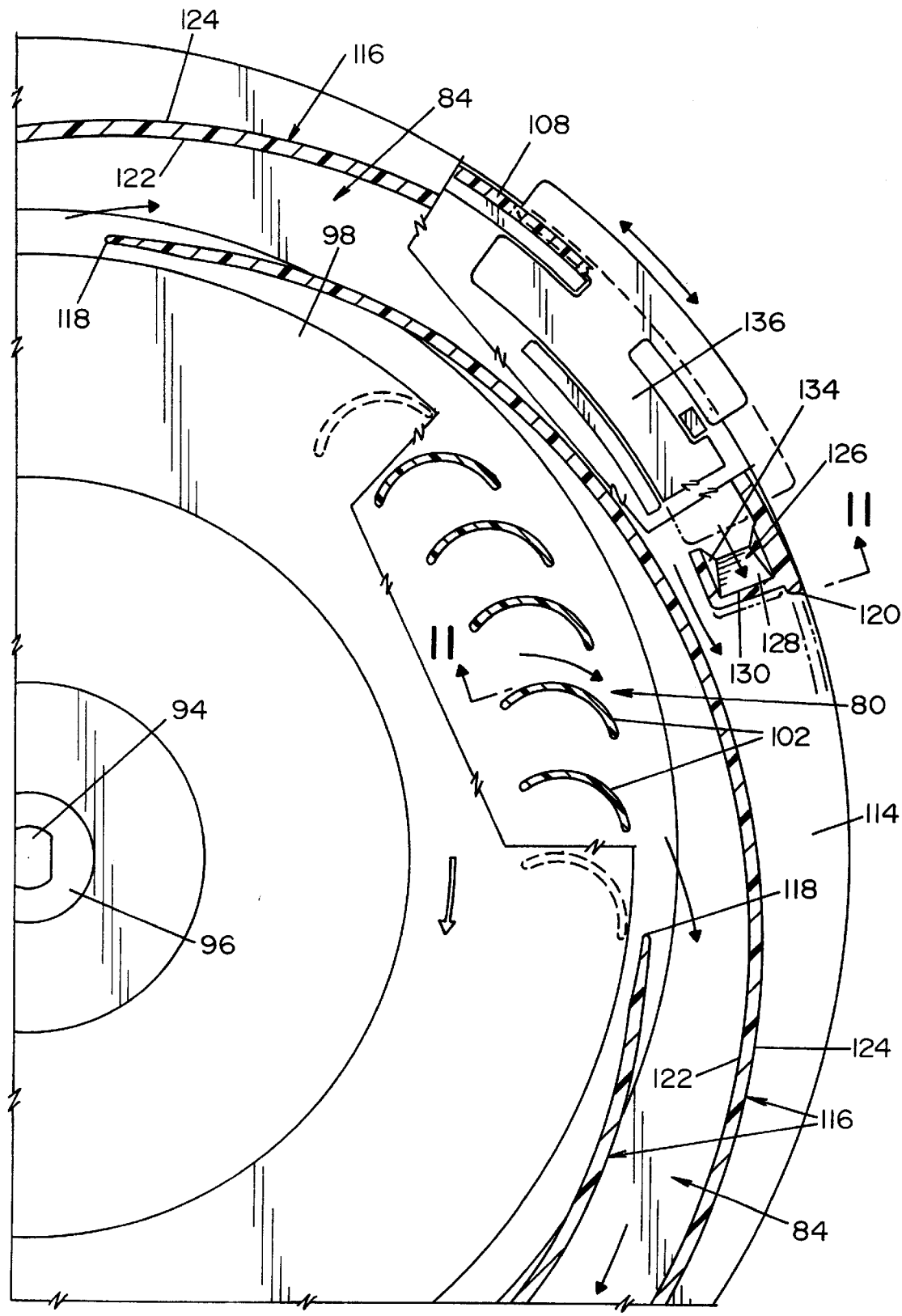
FIG. 10 is a cross-sectional top plan view taken along line 10—10 in FIG. 2; and, FIG. 11 is a cross-sectional elevation view taken along line 11—11 in FIG. 10.
Figure 11:
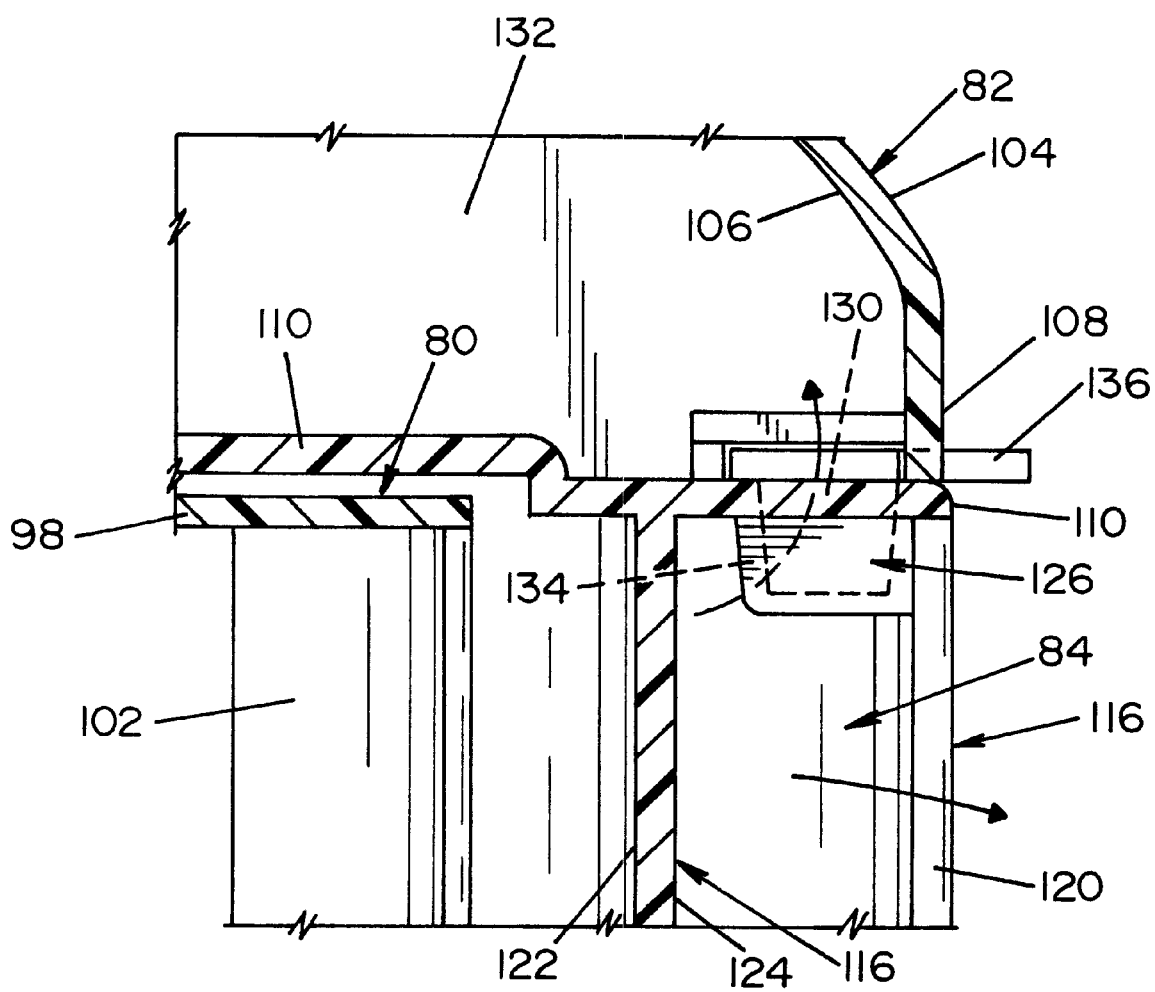

As is more clearly shown in FIGS. 2, 10 and 11, scent discharge passage 86 is fed by a portion of the filtered air being expelled through exhaust passage 84. Diversion channel 126 extends from the fan side of baffle mounting plate 110 into one of the individual passages of exhaust passage 84. Diversion channel 126 has a bottom surface 128 which extends from baffle mounting plate 110 at an acute angle forming a ramp, which diverts filtered air flowing through exhaust passage 84 up the ramp and through baffle plate opening 130, which defines the beginning of scent passage 86, and into scent chamber 132. Extending from bottom surface 128 of diversion channel 126 is channel wall 134. As can be appreciated, diversion channel 126 is defined by bottom surface 128 and may have a channel wall projecting from each side of bottom surface 128 and extending to baffle mounting plate 110. Alternatively, as is shown in FIGS. 10 and 11, bottom surface 128 may be adjacent one of the sides 122 or 124 of one of arcuate vanes 116. In such an embodiment, arcuate vane 116 defines the second wall of diversion channel 126 opposite channel wall 134. Irrespective of the particular embodiment of diversion channel 126, as discussed immediately above, the channel will terminate at baffle mounting plate 110 adjacent at least a portion of baffle plate opening 130 so that diverted air will be in fluid communication with scent chamber 132.

The amount of air diverted which can be channeled through scent discharge passage 86 is directly controlled by baffle 136, best shown in FIGS. 3, 6, 10, and 11. Baffle 136 is slidable between a first position in which the baffle plate opening 130 is largely uncovered, and a second position in which the baffle plate opening is fully covered. Baffle 136 is infinitely adjustable between the first and second positions, providing control over the amount of air flowing through baffle plate opening 130 and into scent chamber 132 and through scent discharge passage 86.

Figure 4:
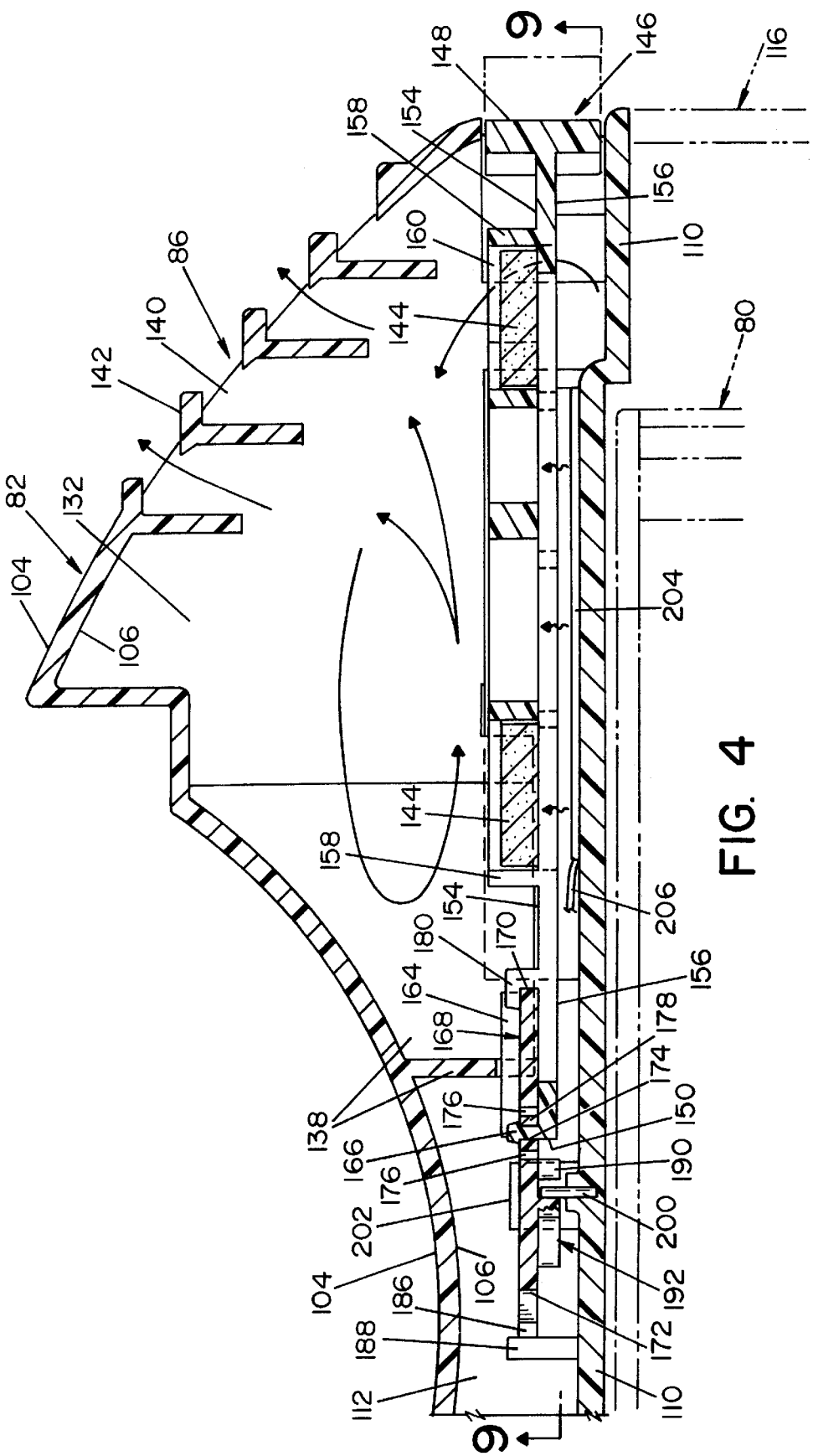
FIG. 4 is a cross-sectional elevation view taken along line 4—4 in FIG. 3.

Scent chamber 132 extends between baffle mounting plate 110 and cover interior surface 106 of cover 82. However, scent chamber 132 is partitioned from cavity 112, also defined therebetween, by chamber wall 138 which defines three sides of the scent chamber. The top and fourth side of scent chamber 132 are defined by cover interior surface 106 of cover 82, and the bottom of scent chamber 132 is defined by baffle mounting plate 110. As is best shown in FIGS. 1 and 4, scent discharge passage 86 ends at cover discharge opening 140 which extends through cover 82 adjacent scent chamber 132. Extending across covered discharge opening 140 is a plurality of louvers 142.

As previously discussed, a portion of the filtered air flowing through exhaust passage 84 is diverted by diversion channel 126, and enters scent discharge passage 86 through baffle plate opening 130, the functional size of which may be reduced by baffle 136. The air entering scent chamber 132 circulates around the chamber as the air is pushed up toward and out of cover discharge opening 140. As the air swirls and circulates through scent chamber 130, the air picks up a freshening scent which is being produced by scent element 144. Drawer 146 is slidably positioned within scent chamber 132, and contains scent element 144. Drawer 146 is slidable between a retracted position, in which drawer 146 and scent element 144 are secured within scent chamber 132, and an ejected position in which drawer 146 and scent element 144 are extending out of upper housing portion 14. With drawer 146 in the ejected position, scent element 144 is accessible such that a used scent element can be easily removed from drawer 146 and replaced with a new scent element.

As is best shown in FIGS. 7, 8, and 9A–9F, drawer 146 has a front end 148, a latch end 150 opposite the front end, a pair of spaced apart sides 152, a top 154, and a bottom 156. Extending vertically from top 154 are retaining walls 158 which form scent element cavity 160 adjacent top 154 of drawer 146. Front end 148 is adjacent and flush with cover exterior surface 104 of cover 82 when drawer 146 is in the retracted position. Bottom 156 of drawer 146 is oriented toward, but spaced away from baffle mounting plate 110. Drawer 146 is longitudinally slidably supported by drawer supports 162 which are positioned adjacent sides 152, and which retain drawer 146 preventing lateral and vertical movement relative to baffle mounting plate 110. Latch end 150 of drawer 146 has two plate retaining tabs 180 projecting from top 154 of drawer 146 at latch end 150. Additionally, two spring reaction walls 164 extend longitudinally from latch end 150 toward front end 148, and retaining barb 166 is centered therebetween at latch end 150. Latch plate 168 has a tab end 170 and a spring end 172, and is oriented such that tab end 170 is toward front end 148 of drawer 146. Latch plate 168 has a laterally oriented plate retaining slot 174 with two laterally oriented deflection slots 176 longitudinally positioned adjacent retaining slot 174, forming deflection bars 178 therebetween. Latch plate 168 is attached to latch end 150 of drawer 146 by positioning tab end 170 underneath plate retaining tabs 180, and forcing plate retaining slot 174 over retaining barb 166. Deflection bars 178 are forced away from plate retaining slot 174 and into deflection slots 176, allowing retaining barb 166 to pass through plate retaining slot 174 before returning to an undeflected position thereby preventing the removal of latch plate 168. A first spring 182 is attached to and acts to transversely bias latch plate 168 by acting against spring reaction wall 164. A second spring 184 is attached to latch plate 168 opposite first spring 182 and acts to transversely bias latch plate 168 in the opposite direction from first spring 182 by acting on a second spring reaction wall 164. As a result of the bias of both springs acting opposite each other, latch plate 168 can slide laterally along plate retaining slot 174 in either lateral direction, but latch plate 168 will return to the transverse center of drawer 146 as the spring biases balance against one another. Latch plate 168 includes a third spring 186 attached at the spring end 172. Third spring 186 biases drawer 146 toward an ejected position by acting against a spring reaction wall 188 extending from baffle mounting plate 110. In a preferred alternative spring construction, spring 186 is replaced by two leaf spring, one extending from the top spring 182 and one from the top of spring 184. These leaf springs converge at bulbous ends riding on reaction wall 188. This reduces the transverse frictional force between the spring construction and reaction wall 188. Latch plate 168 has a first boss 190 and a second boss 192 protruding downwardly therefrom. Projecting upwardly from baffle mounting plate 110 is latch post 200 which is positioned adjacent first and second bosses, 190 and 192 respectively, when drawer 146 is in the retracted position.

Figure 9A:
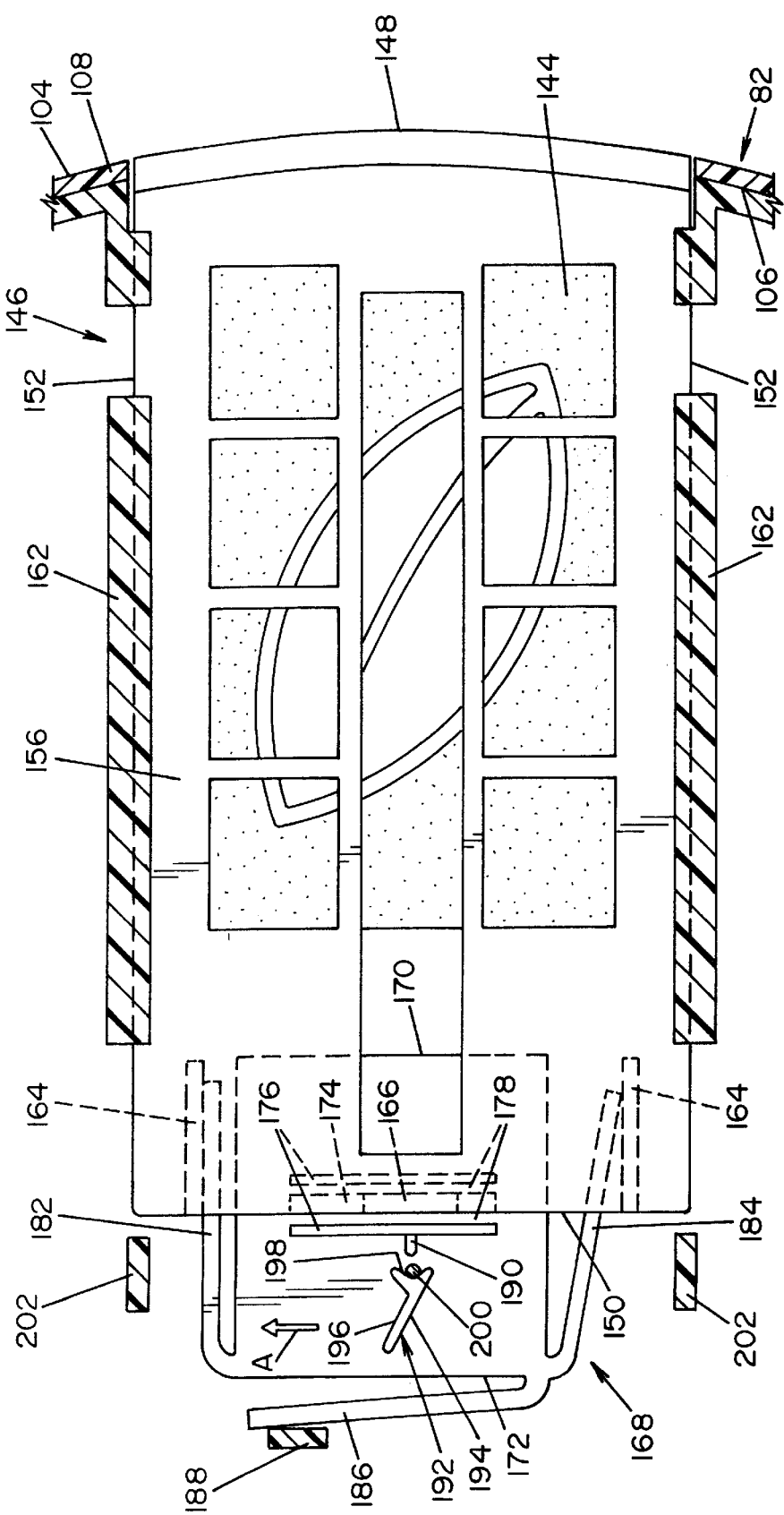
FIG. 9A is a cross-sectional, bottom plan view of the drawer, latch mechanism, and scent element taken along line 9—9 in FIG. 4, and showing the drawer, latch mechanism, and scent element retracted with the latch plate laterally positioned.

A previously discussed object of the subject invention is the provision of an air filtering and freshening device 10 in which scent element 144 can be easily accessed and replaced without the need for tools. FIGS. 9A–9F illustrate a mechanism by which this object is accomplished. FIG. 9A shows a bottom view of drawer 146 secured in retracted position with latch post 200 engaging holding portion 198 of second boss 192, preventing the ejection of the drawer. In this position, latch plate 168 is biased from center in the direction of arrow A, compressing first spring 182. Additionally, the longitudinal position of drawer 146 and latch plate 168 when latch post 200 is engaging holding portion 198 requires that third spring 186 be compressed against spring reaction wall 188.

Figure 9B:
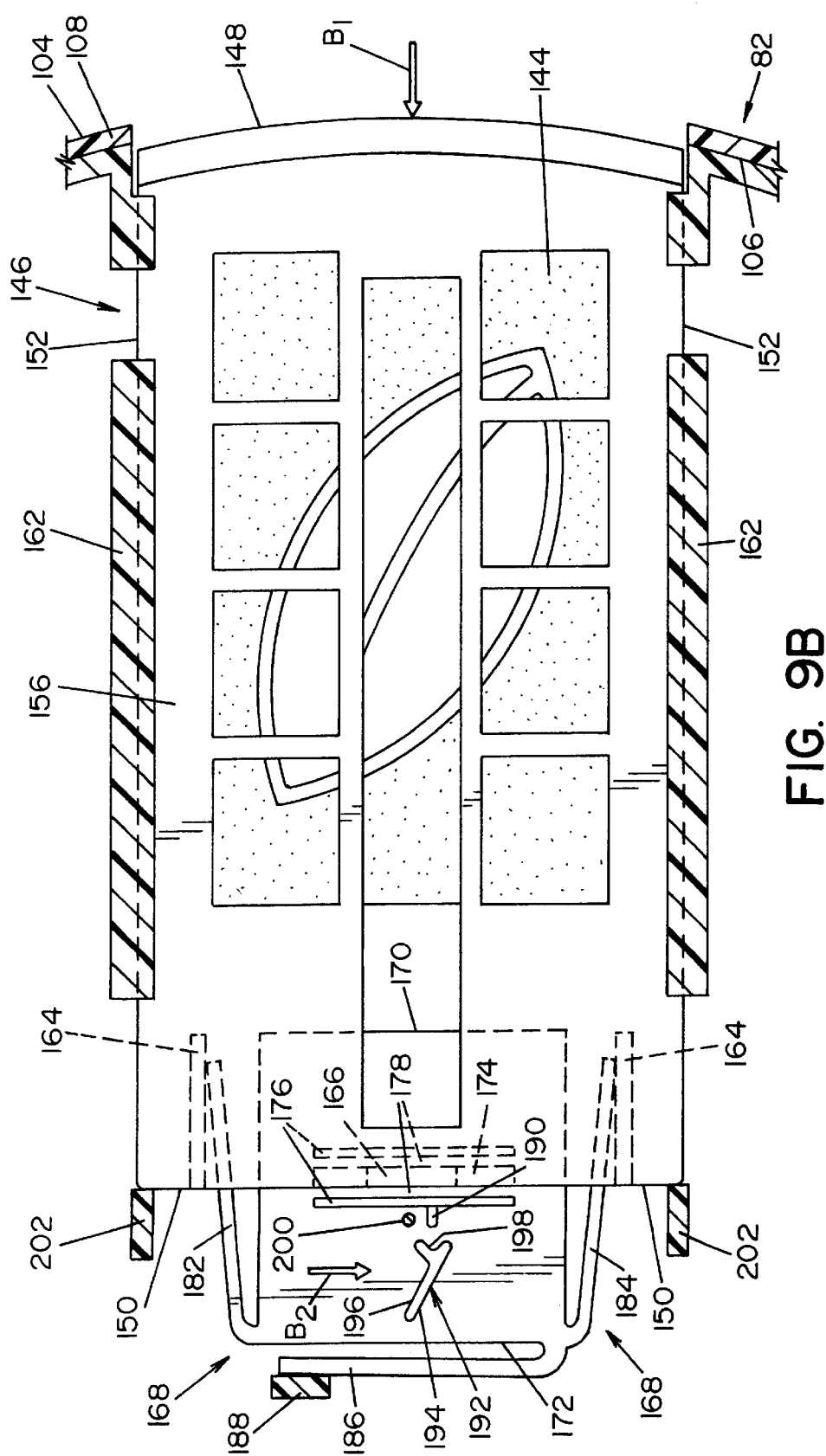
FIG. 9B is a cross-sectional, bottom plan view of the drawer, latch mechanism, and scent element taken along line 9—9 in FIG. 4, and showing the drawer, latch mechanism, and scent element depressed and the latch mechanism centered.
Figure 9C:
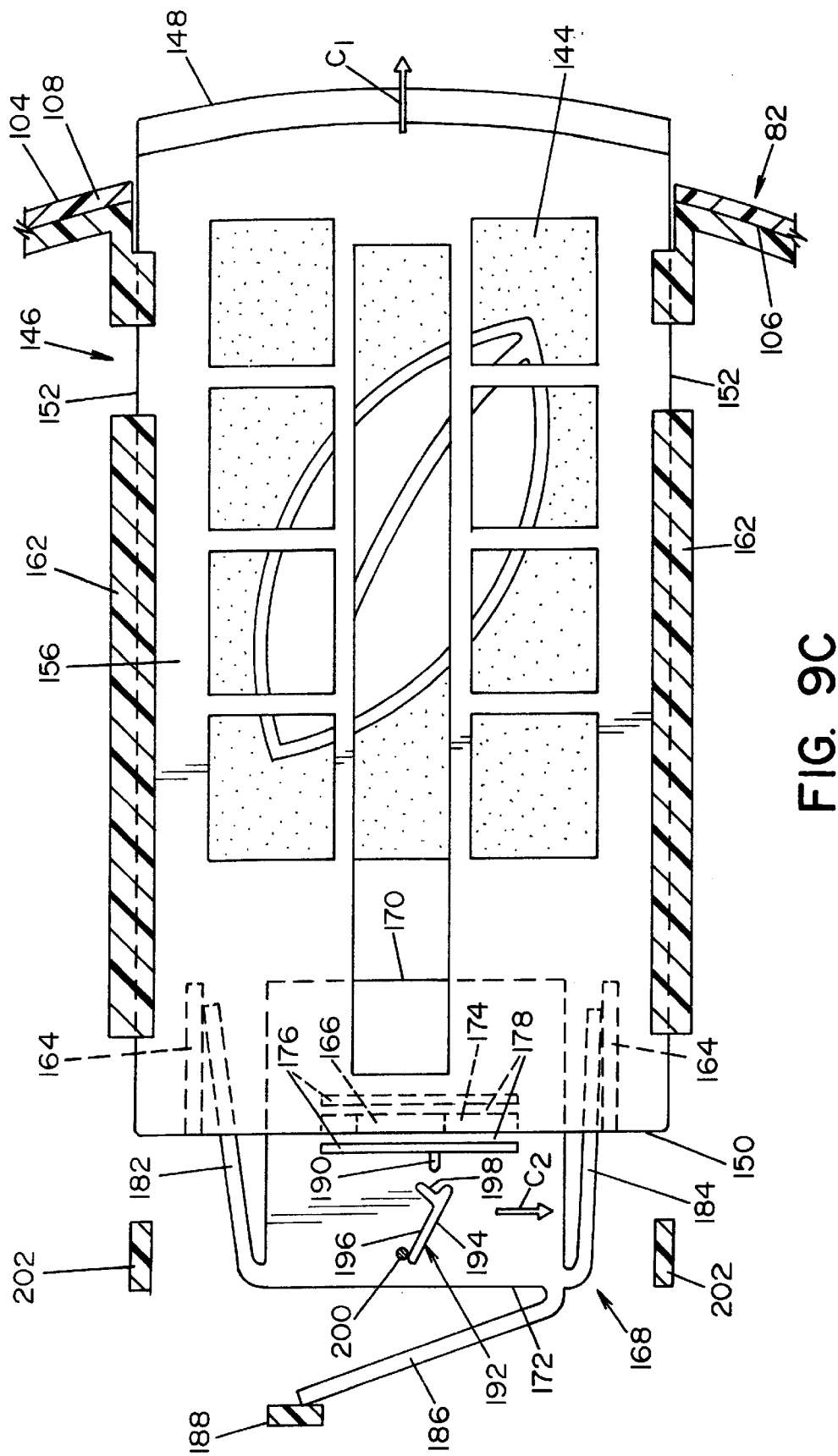
FIG. 9C is a cross-sectional, bottom plan view of the drawer, latch mechanism, and scent element taken along line 9—9 in FIG. 4, and showing the drawer, latch mechanism, and scent element released and the latch mechanism ejecting the drawer.
Figure 9D:
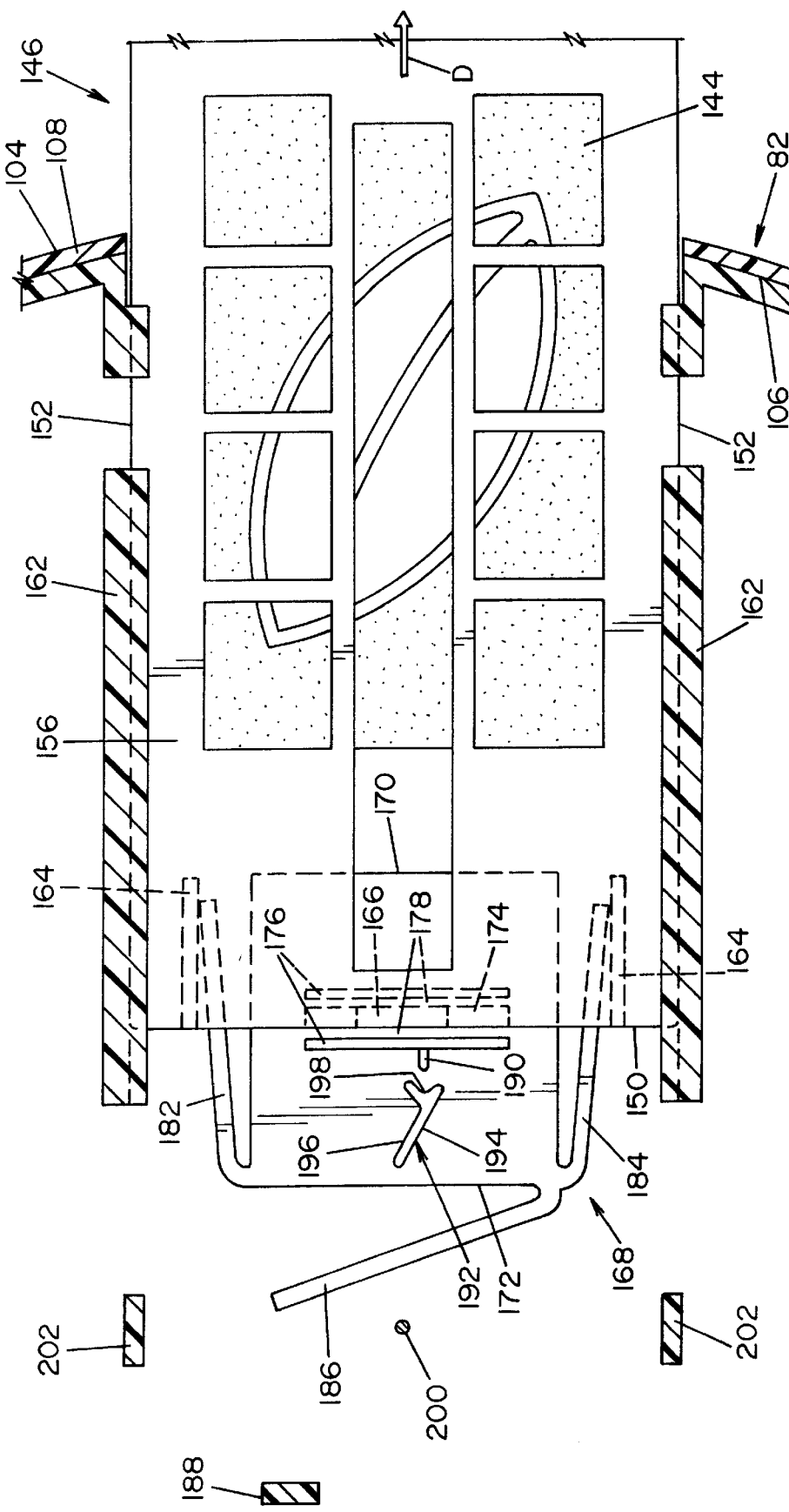
FIG. 9D is a cross-sectional, bottom plan view of the drawer, latch mechanism, and scent element taken along line 9—9 in FIG. 4, and showing the drawer, latch mechanism, and scent element released toward the ejected position.

To eject drawer 146 from within scent chamber 132, drawer 146 must be depressed into scent chamber 132, as indicated by arrow B₁, until latch end 150 contacts drawer stops 202, as shown in FIG. 9B. This action moves holding portion 198 of second boss 192 longitudinally away from latch post 200, allowing compressed first spring 182 to center latch plate 168 on drawer 146, as indicated by arrow B₂. First boss 190 is positioned longitudinally adjacent second boss 192 opposite holding portion 198. As drawer 146 is forced into scent chamber 132, first boss 190 assists first spring 182 in moving latch plate 168 to a center position in which latch post 200 is laterally adjacent second boss 192. At this point, as can be in FIGS. 9C and 9D, the depression force is eliminated, and third spring 186 biases drawer 146 toward the ejected position, as indicated by arrow C₁, during which time, ejecting portion 196 of second boss 192 can pass beside or slide against latch post 200. As is best shown in FIG. 9C, ejecting portion 196 of second boss 192 compresses second spring 184, as indicated by arrow C₂, as ejecting portion 196 slides past latch post 200. As is then shown in FIG. 9D, as drawer 146 moves toward the ejected position, as indicated by arrow D, and the influence of latch post 200 on ejecting portion 196 has been discontinued, the compressive force on second spring 184 has dissipated and latch plate 168 has been again centered on drawer 146 as the bias forces of second spring 184 and first spring 182 balance against each other.

Figure 9E:
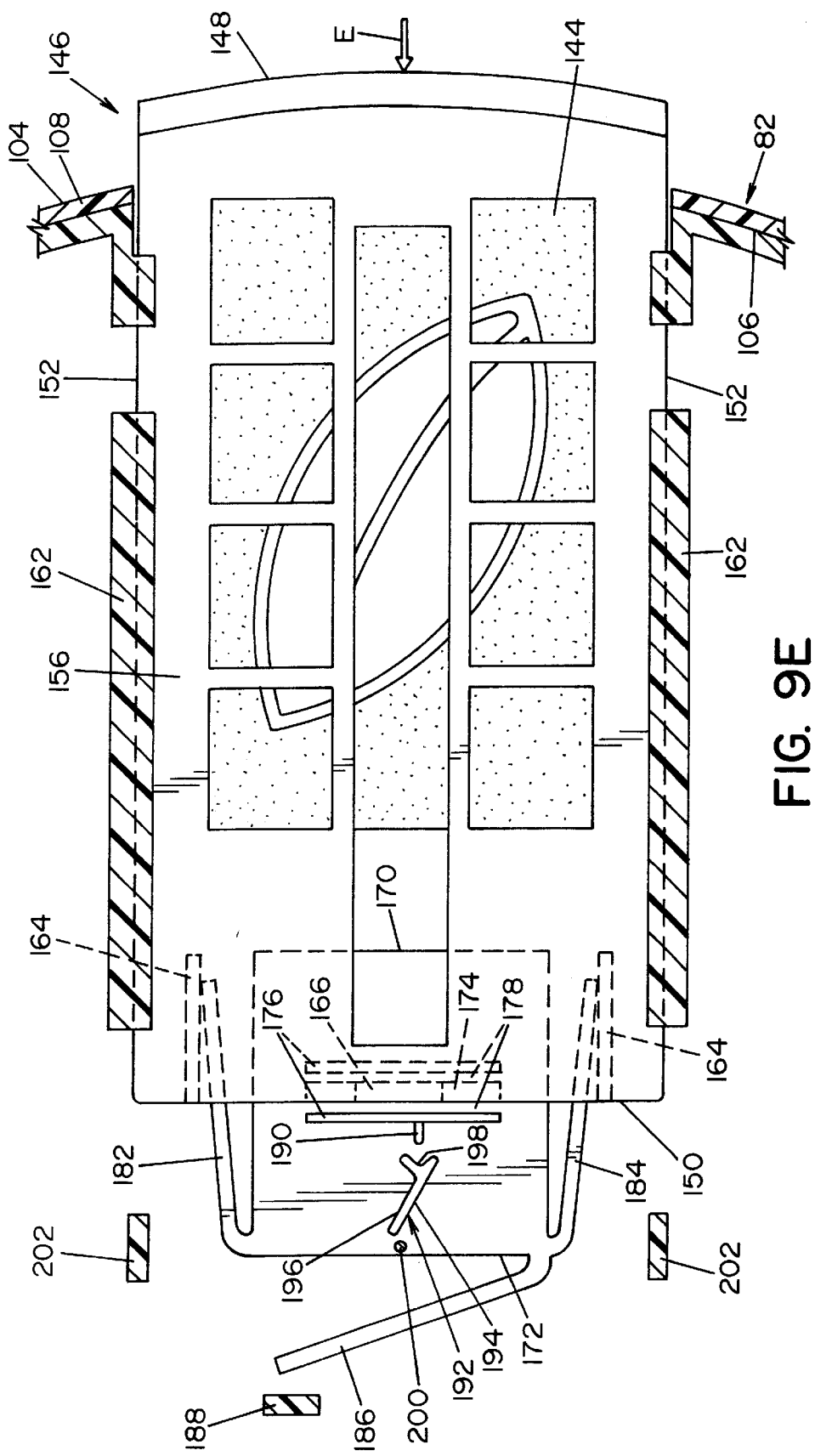
FIG. 9E is a cross-sectional, bottom plan view of the drawer, latch mechanism, and scent element taken along line 9—9 in FIG. 4, and showing the drawer, latch mechanism, and scent element depressed toward the retracted position.
Figure 9F:
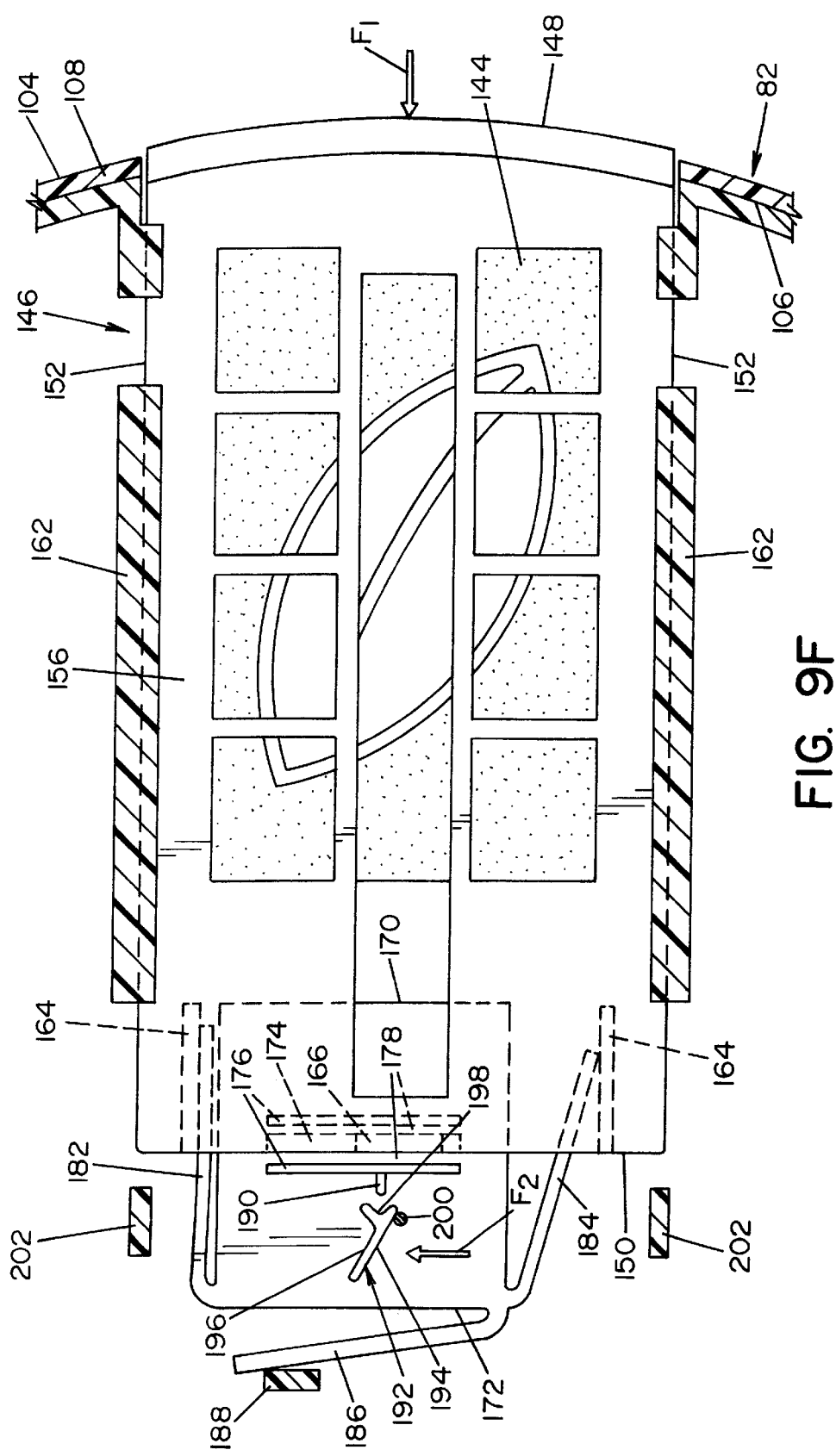
FIG. 9F is a cross-sectional, bottom plan view of the drawer, latch mechanism, and scent element taken along line 9—9 in FIG. 4, and showing the drawer, latch mechanism, and scent element depressed toward the retracted position with the latch mechanism transversely positioned.

Having been ejected from scent chamber 132 and with scent element 144 replaced, drawer 146 is depressed toward the retracted position, as is shown in FIG. 9E and indicated by arrow E, in which latch post 200 will be positioned longitudinally adjacent holding portion 198 of second boss 192, shown in FIGS. 9F and 9A. As indicated by arrows E and F, of FIGS. 9E and 9F respectively, retracting portion 194 of second boss 192 approaches and slideably engages latch post 200 as drawer 146 moves toward the retracted position. Correspondingly, this movement laterally biases latch plate 168 compressing first spring 182 as indicated by arrow F₂ of FIG. 9F. Retracting portion 194 slides along latch post 200 until reaching holding portion 198, at which point the biasing force from retracting portion 194 dissipates. Compressed first spring 182 will attempt to relieve the compression force by moving latch plate 168 toward the center of drawer 146, and thereby causing holding portion 198 of second boss 192 to engage latch post 200. Furthermore, as drawer 146 is being longitudinally depressed into the retracted position, third spring 186 will contact spring reaction wall 188 slightly compressing third spring 186 in preparation for the next ejection cycle, beginning again with FIG. 9A.

Figure 5:
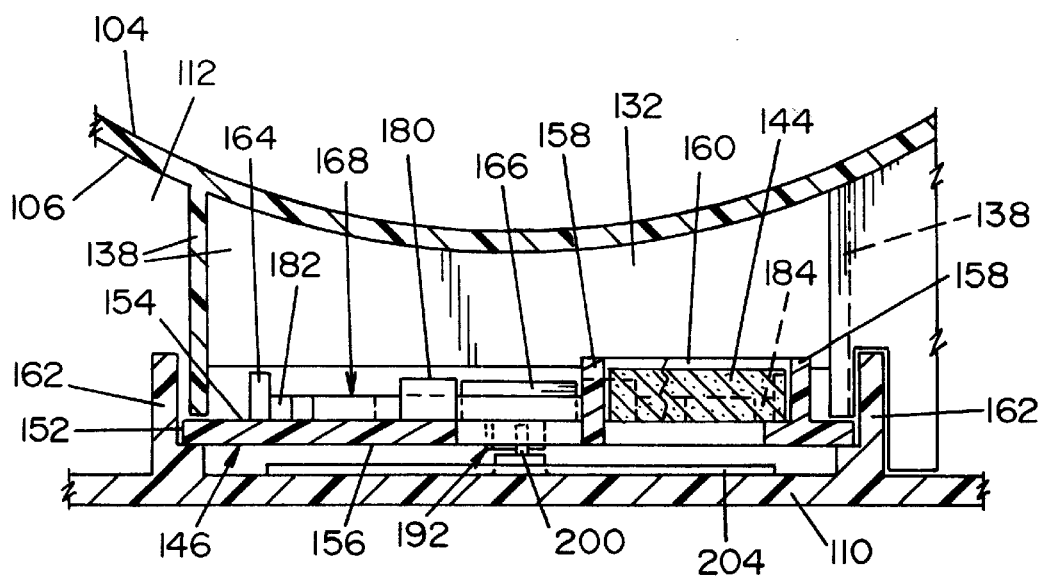
FIG. 5 is a cross-sectional elevation view taken along line 5—5 in FIG. 3.
Figure 6:
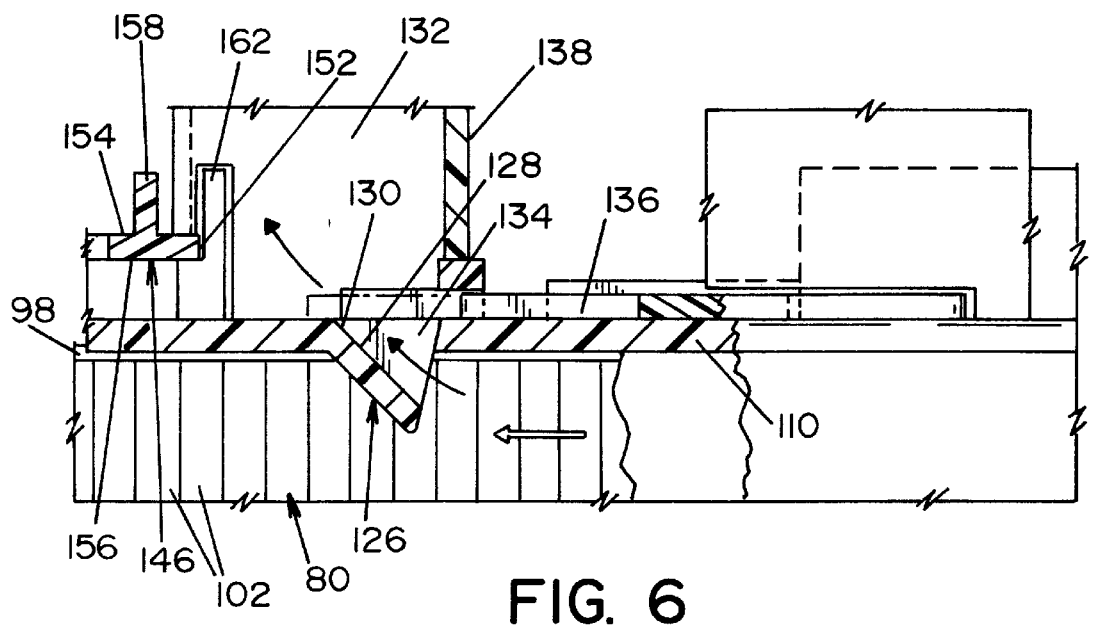
FIG. 6 is a cross-sectional elevation view taken along line 6—6 in FIG. 3.
Figure 7:
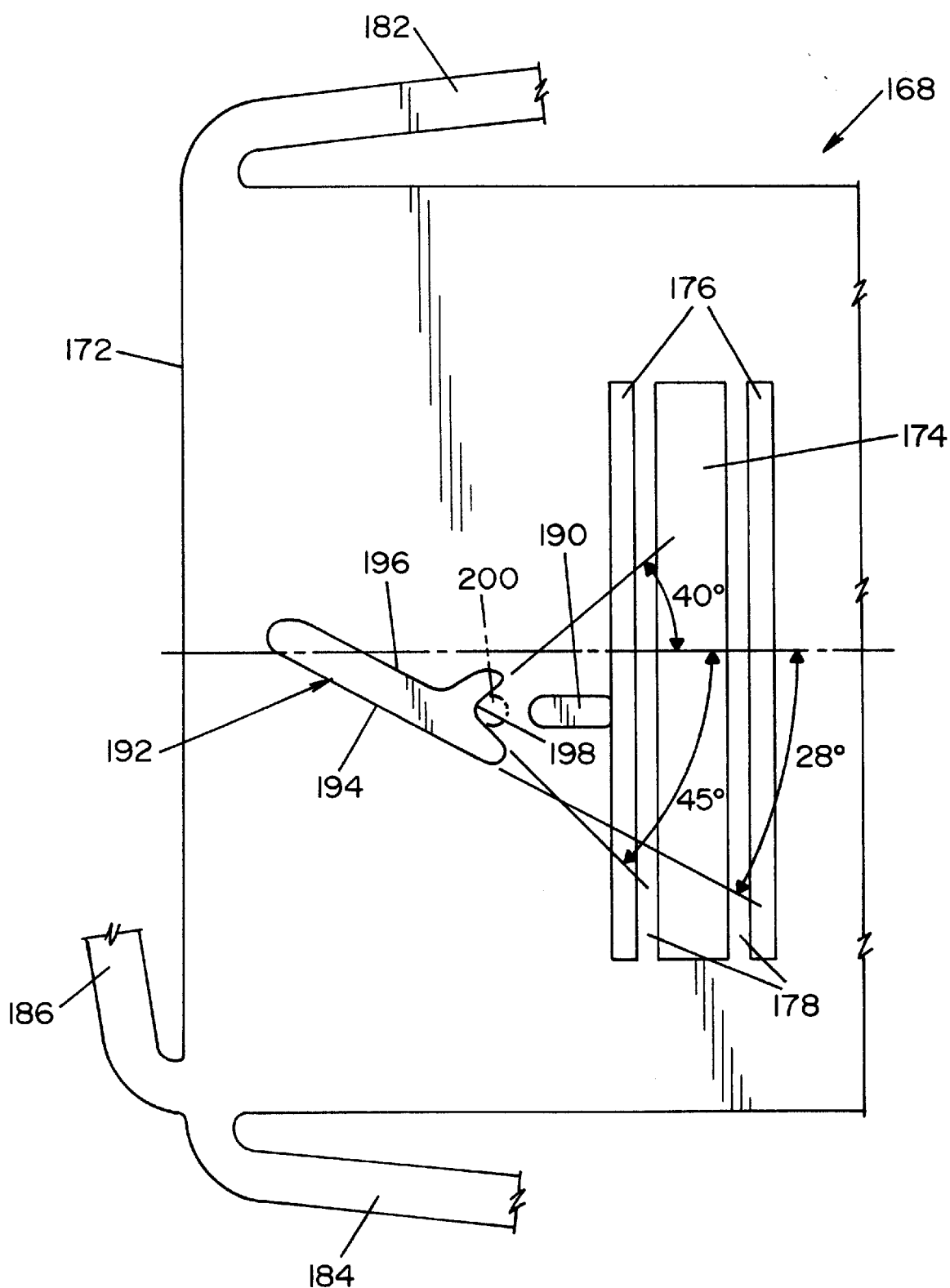
FIG. 7 is a bottom plan view of the latch mechanism shown in FIG. 3.
Figure 8:
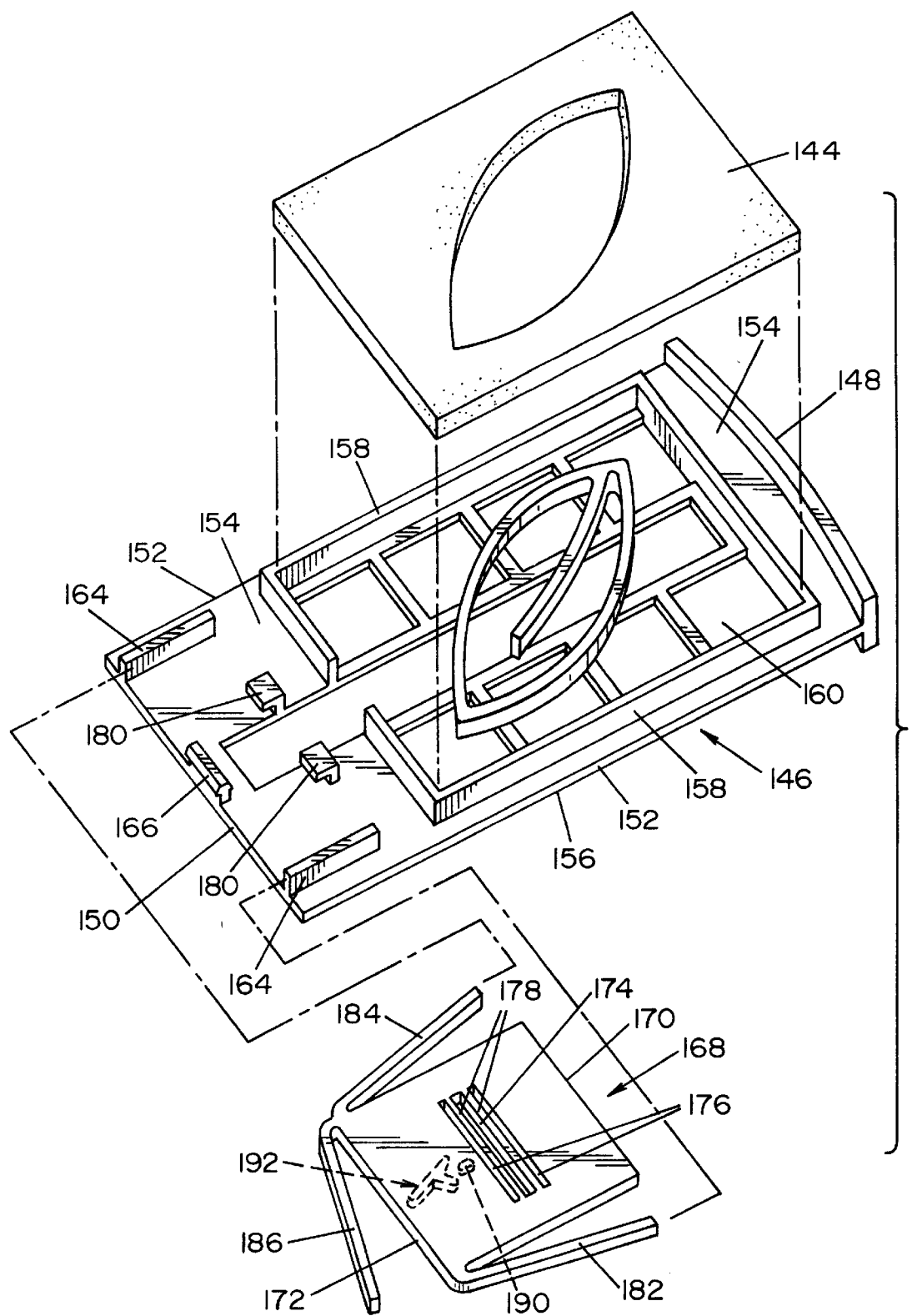
FIG. 8 is an exploded perspective view of the drawer, latch mechanism, and scent element shown in FIG. 3.

To further enhance the effectiveness and output of scent discharge passage 86, a heating element 204 is positioned subjacent scent element 144 and drawer 146, as shown best in FIGS. 4 and 5. Heating element 204 receives electric current through wire 206 which causes an increase in the temperature of heating element 204 in a conventional manner. Heating element 204 warms scent element 144 increasing the freshening scent output therefrom. The increased freshening scent is carried out of the scent chamber 132 through cover discharge opening in the manner describe hereinbefore, increasing the overall effectiveness of scent discharge passage 86.

Heating element 204 receives electric current through wire 206, as previously described. The current is controlled through heater switch 208, as can best be seen in FIGS. 1 and 2. Heater switch 208 is electrically connected to control box 214, which includes fan speed control 210. Control box 214 receives electrical power through electrical cord 216 which is adaptable to connect to a typical electrical receptacle (not shown) using a typical electrical plug (not shown). Between control box 214 and the electrical plug, electrical cord 216 connects with motor 78, and also includes a filter change plug 212. As filter element 38 becomes dirty and contaminated, it is necessary to separate the upper housing portion 14 from lower housing portion 12 to replace filter element 38. A filter change plug 212 can be used to disconnect the electrical cord 216, as is further described in Cartellone ('020). However, electrical cord 216 may also be wired directly into upper housing portion 14 obviating the need for filter change plug 212.

Having thus described the invention, it is so claimed:

1. An air filtering and freshening device, comprising:

a housing having an air inlet and an air outlet;

a motor within said housing between said air inlet and said air outlet;

a filter element at said air inlet for removing contaminants from incoming air;

a fan driveably connected to said motor for drawing a set volumetric flow of air from said air inlet through said filter element and out said air outlet;

said air outlet having an exhaust passage and a scent discharge passage, each passage being in fluid communication with said fan; and, a freshening device within said scent discharge passage for delivering freshening scent into air flowing through said scent discharge.

2. The air filtering and freshening device of claim 1, wherein said housing has a lower portion and an upper portion;

said lower portion including a base and a motor mount, said motor mount being axially spaced from said base defining a gap therebetween forming said air inlet, said motor mount having an inside surface which has a filter support surface portion facing said base, and an outside surface opposite said inside surface having a motor mount surface portion and a vane mount surface portion radially outward said motor mount surface portion;

said filter element extending between said filter support surface and said base;

said upper portion of said housing extending from said outside surface of said motor mount and including a cover, a baffle mounting plate, and a plurality of arcuate vanes, said cover having an exterior surface, an interior surface, a discharge vent, and a peripheral edge, said baffle mounting plate being adjacent said peripheral edge of said cover and having a top surface toward said interior surface of said cover forming a scent chamber therebetween, said discharge vent of said cover being adjacent said scent chamber and in fluid communication therewith, and said baffle mounting plate having a bottom surface opposite said top surface, said bottom surface of said baffle mounting plate being axially spaced from said vane mounting surface portion of said motor mount forming a gap therebetween, said plurality of arcuate vanes extending from said bottom surface of said baffle mounting plate across said gap and terminating adjacent said vane mount surface portion defining said exhaust passage extending between adjacent vanes; and, said baffle mounting plate having a scent opening therethrough, whereby said scent chamber is in fluid communication with said fan, said scent passage extending from said scent opening through said scent chamber to said discharge vent, and said baffle mounting plate including a diversion channel extending from said bottom surface adjacent said scent opening and into said exhaust passage between said plurality of arcuate vanes.

3. The air filtering and freshening device of claim 2, wherein said plurality of arcuate vanes each have a leading end, a trailing end downstream of said leading end, a concave surface, and a convex surface opposite said concave surface, said diversion channel being radially positioned on said bottom surface of said baffle mounting plate adjacent said trailing end of one of said plurality of arcuate vanes.

4. An air filtering and freshening device of claim 3, wherein said diversion channel is radially positioned adjacent said concave surface of said one of said plurality of arcuate vanes.

5. The air filtering and freshening device of claim 4, wherein said leading end of each of said plurality of arcuate vanes is adjacent said fan.

6. The air filtering and freshening device of claim 2, wherein said freshening device further includes a baffle moveable relative to said wall top surface of said inside wall adjacent and pivotable over said opening between a first position and a second position.

7. The air filtering and freshening device of claim 6, wherein said freshening device further includes a drawer, said drawer having a front end, a latch end opposite said front end, a top, a bottom, and a pair of spaced apart sides, said drawer having a retaining cavity adjacent said top for retaining said scent element, said drawer being positioned within said scent chamber and moveable between a retracted position and an ejected position, said drawer being oriented such that said bottom said drawer is adjacent said top surface of said baffle mounting plate and said front end is toward said exterior surface of said cover of said housing.

8. The air filtering and freshening device of claim 7, wherein the freshening device includes a latch mechanism, said latch mechanism includes a latch plate, a first spring, a second spring, a third spring, and a retaining pin, said drawer having a longitudinal centerline extending in said direction of travel of said drawer and a transverse centerline perpendicular to said longitudinal centerline, said latch plate being slidably attached to said drawer adjacent said latch end for transverse movement relative thereto, said latch plate having a boss extending therefrom toward said bottom of said drawer, said first spring biasing said latch plate in a direction parallel with said transverse centerline, said second spring biasing said latch plate in a direction parallel with said transverse centerline and opposite said first spring, said third spring biasing said latch plate parallel with said longitudinal centerline toward said extended position, and said retaining pin extending from said top surface of said baffle mounting plate for engaging said boss in said retracted position.

9. The air filtering and freshening device of claim 8, wherein said freshening device further includes a heating element for warming said scent element, said heating element being positioned within said scent discharge passage between said bottom of said drawer and said top surface of said baffle mounting plate.

10. An air filtering and freshening device, comprising:
a housing having an air inlet and an air outlet;
a motorized fan between said air inlet and said air outlet;
filter means adjacent said air inlet and upstream of said motorized fan; and, a freshening device adjacent said air outlet and downstream of said motorized fan, said air outlet including an exhaust passage for discharging filtered air and a separate scent discharge passage for discharging filtered and freshened air.

11. The air filtering and freshening device of claim 10, wherein said freshening device includes a diversion channel adjacent said scent discharge passage.

12. The air filtering and freshening device of claim 10, wherein said freshening device includes a baffle adjacent said scent discharge passage.

13. The air filtering and freshening device of claim 10, wherein said freshening device includes a scent element adjacent said scent discharge passage.

14. The air filtering and freshening device of claim 13, wherein said freshening device includes heating means adjacent said scent element.

15. An air filtering and freshening device, comprising:
a housing having an air inlet and an air outlet;
a motorized fan between said air inlet and said air outlet;
a filter positioned between said air inlet and said motorized fan;
a freshening device adjacent said air outlet and downstream of said motorized fan, said freshening device only partially exposed to air passing through said air outlet; and,
said air outlet includes an exhaust passage and a scent discharge passage, each passage being in fluid communication with said fan, said scent discharge passage forming at least a portion of said freshening device.

16. The air filtering and freshening device as defined in claim 15, said scent discharge passage includes an air flow control baffle.

17. The air filtering and freshening device as defined in claim 16, wherein said air flow control baffle is adjustable.

18. The air filtering and freshening device as defined in claim 16, including a heater to at least partially heat said freshening device.

19. The air filtering and freshening device as defined in claim 17, including a heater to at least partially heat said freshening device.

20. The air filtering and freshening device as defined in claim 17, wherein said freshening device further includes a drawer to provide access to at least one component in said freshening device, said drawer moveable between a retracted position and an ejected position. device further includes a drawer to provide access to at least one component in said freshening device, said drawer movable between a retracted position and an ejected position.

21. The filtering and freshening device as defined in claim 19, wherein said freshening device further includes a drawer to provide access to at least one component in said freshening device, said drawer movable between a retracted position and an ejected position.

22. An air filtering and freshening device, comprising:
a housing having an air inlet and an air outlet;
a motorized fan between said air inlet and said air outlet;
a filter positioned between said air inlet and said motorized fan;
a freshening device adjacent said air outlet and downstream of said motorized fan, said freshening device including a heater to at least partially heat said freshening device; and
said freshening device further includes a drawer to provide access to at least one component in said freshening device, said drawer moveable between a retracted position and an ejected position.

23. An air filtering and freshening device, comprising:
a housing having an air inlet and an air outlet;
a motorized fan between said air inlet and said air outlet;

a filter positioned between said air inlet and said motorized fan; and, a freshening device adjacent said air outlet and downstream of said motorized fan, said freshening device including an adjustable air flow control baffle to control the flow through said freshening device.

24. The air filtering and freshening device as defined in claim 23, wherein said freshening device only partially exposed to air passing through said air outlet.

25. The air filtering and freshening device as defined in claim 24, wherein said air outlet includes an exhaust passage and a scent discharge passage, each passage being in fluid communication with said fan, said scent discharge passage forming at least a portion of said freshening device.

26. An air filtering and freshening device, comprising:

a housing having an air inlet and an air outlet;

a motorized fan between said air inlet and said air outlet;

a filter positioned between said air inlet and said motorized fan;

a freshening device adjacent said air outlet and downstream of said motorized fan, said freshening device including a heater to at least partially heat said freshening device; and said freshening device only partially exposed to air passing through said air outlet.

27. The air filtering and freshening device as defined in claim 26, wherein said air outlet includes an exhaust passage and a scent discharge passage, each passage being in fluid communication with said fan, said scent discharge passage forming at least a portion of said freshening device.

28. An air filtering and freshening device, comprising:

a housing having an air inlet and an air outlet;

a motorized fan between said air inlet and said air outlet;

a filter positioned between said air inlet and said motorized fan; and, a freshening device adjacent said air outlet and downstream of said motorized fan, said freshening device including a drawer to provide access to at least one component in said freshening device, said drawer moveable between a retracted position and an ejected position.

29. The air filtering and freshening device as defined in claim 28, wherein said freshening device only partially exposed to air passing through said air outlet.

30. The air filtering and freshening device as defined in claim 29, wherein said air outlet includes an exhaust passage and a scent discharge passage, each passage being in fluid communication with said fan, said scent discharge passage forming at least a portion of said freshening device.

* * * * *